(12) United States Patent
Martani

(10) Patent No.: US 7,182,959 B2
(45) Date of Patent: Feb. 27, 2007

(54) RAPIDLY DISSOLVING DOSAGE FORM AND PROCESS FOR MAKING SAME

(75) Inventor: Rosa Martani, Divonne-les-Bains (FR)

(73) Assignee: Novartis AG, Nyon (CH)

( * ) Notice: Subject to any disclaimer, the term of this patent is extended or adjusted under 35 U.S.C. 154(b) by 0 days.

(21) Appl. No.: 10/075,429

(22) Filed: Feb. 13, 2002

(65) Prior Publication Data

US 2002/0131998 A1 Sep. 19, 2002

Related U.S. Application Data

(63) Continuation of application No. PCT/EP00/07934, filed on Aug. 14, 2000.

(30) Foreign Application Priority Data

Aug. 17, 1999 (EP) .................................. 99810738

(51) Int. Cl.
*A61K 9/20* (2006.01)
*B29B 9/00* (2006.01)
*B29D 11/00* (2006.01)

(52) U.S. Cl. .......................... 424/464; 424/465; 424/4

(58) Field of Classification Search ................ 424/400, 424/489, 464, 465, 468, 493, 462, 499, 467, 424/490

See application file for complete search history.

(56) References Cited

U.S. PATENT DOCUMENTS

| | | | |
|---|---|---|---|
| 4,311,490 A * | 1/1982 | Bovenkerk et al. ............ 51/307 |
| 5,108,757 A * | 4/1992 | Erdos et al. ................. 424/451 |
| 5,686,107 A | 11/1997 | Ratnaraj et al. | |
| 6,083,531 A * | 7/2000 | Humbert-Droz et al. .... 424/464 |
| 6,194,395 B1 * | 2/2001 | Schultz et al. ................ 514/58 |

FOREIGN PATENT DOCUMENTS

| | | | |
|---|---|---|---|
| EP | 0 084 705 A2 | | 11/1982 |
| EP | 0 651 997 A1 | | 12/1992 |
| EP | 0 651 997 | * | 5/1995 |
| EP | 0 839 526 A2 | | 10/1997 |
| EP | 0 839 526 | * | 5/1998 |
| WO | WO 91/15194 | | 2/1991 |
| WO | WO 92/21328 | | 5/1992 |
| WO | WO 92/21328 | * | 12/1992 |
| WO | WO 97/38679 | | 4/1997 |
| WO | WO 97/38679 | * | 10/1997 |
| WO | WO 97/38679 A2 | * | 10/1997 |
| WO | WO 99/17748 | | 9/1998 |

OTHER PUBLICATIONS

The Merk Index, Ninth Edition, p. 996, 1976.*
Ansel et al., "Pharmaceutical Dosage Forms and Drug Delivery Systems", seventh edition, 1995, p. 209.*
European Search Report.
International Search Report.
Kibbe Ah et al., (Ed.), "Povidone", Handbook of Pharmaceutical Excipients, 3rd ed., 2000, American Pharmaceutical Association, Washington, DC, Pharmaceutical Press, London [XP-002155900].

* cited by examiner

*Primary Examiner*—S. Tran
(74) *Attorney, Agent, or Firm*—Diane E. Furman; E. Jay Wilusz; John W. Kung

(57) ABSTRACT

The invention relates to a solid dosage form which is rapidly disintegrating in aqueous medium. Especially, the invention relates to pharmaceutical, orally ingested solid dosage forms, which are designed to disintegrate rapidly within the mouth, and to analogous veterinary dosage forms. Moreover, the invention relates to a unique process for the manufacture of said solid dosage forms.

9 Claims, No Drawings

RAPIDLY DISSOLVING DOSAGE FORM AND PROCESS FOR MAKING SAME

This application is a continuation of International PCT Patent Application No. PCT/EP00/07934, filed Aug. 14, 2000, which in its entirety is herein incorporated by reference.

The present invention relates to the field of solid, rapidly dissolving dosage forms. Wherever a solid dosage form comprising any kind of active ingredient and bound to dissolve rapidly in an aqueous medium is needed, the unique dosage forms provided by the present invention may be applied.

In the first instance, the invention relates to pharmaceutical, orally ingested solid dosage forms, which are designed to dissolve rapidly within the mouth. Another preferred field of applying the invention is solid, rapidly dissolving dosage forms which are administered orally to animals, especially mammals like e.g. dogs, cats, horses or cattle, e.g. veterinary dosage forms.

In the pharmaceutical field, there is a great need for said dosage forms because many people are unwilling and/or unable to swallow tablets, capsules and other traditional solid dosage forms. The present invention provides a solid pharmaceutical dosage form adapted for direct oral administration, i.e. for direct insertion into the mouth of a patient. This is particularly useful in administration of medicaments to e.g. children, debilitated patients, patients who have difficulty swallowing solids and the elderly.

Currently the main technologies to obtain such type of dosage forms are: (1) The active ingredient is mixed with water-soluble diluents and compressed on a tableting machine at low to medium compression force. (2) A suspension is prepared from the active ingredient and appropriate excipients, which suspension is then dispensed into blister packs and finally dried, for example freeze-dried (e.g. Zydis®).

All these technologies have their drawbacks: For example in the case of (1), the mechanical resistance of the dosage forms is often insufficient in normal blister packs and the dosage forms often do not disintegrate rapidly enough (time needed for dissolution may be up to 60 seconds and more). In the case of (2), again lacking mechanical resistance in normal blister packs can be a problem but in particular the time-consuming and costly freeze-drying process is a major disadvantage. Moreover, the effectiveness of a freeze-drying process always depends on the physico-chemical parameters of the active substances used. For certain active substances, especially such having a high solubility in water, it is therefore difficult or impossible to apply a freeze-drying process and consequently this technology. Finally, the development of units with high doses (up to 500 mg or even 1000 mg) of active ingredients and/or combinations of active ingredients may be difficult or even impossible with this technology.

The present invention addresses the needs mentioned above and the problems encountered with currently available technologies. The expensive freeze-drying process is avoided. The manufacture of the dosage form of the invention is simple and suitable for a broad range of active ingredients with different physico-chemical parameters, for high dose unit forms (up to e.g. 1000 mg, in particular 500 mg, of active substance) and also for combinations of active ingredients, including combinations of a water-soluble with a water-insoluble active substance. Moreover, it overcomes the main problems of drying suspensions which are filled in blister packs, by (a) assuring that the dosage forms always have a uniform content of the active ingredient(s); (b) assuring that the dosage forms always have a uniform tablet weight (e.g. dose weights accurate within 2–3%); (c) avoiding a time-consuming process for removing high quantities of solvent; (d) allowing easy upscaling of the process developed in the laboratory; and (e) avoiding moisture uptake during storage.

The basis for the new beneficial solid dosage forms is a newly developed advantageous process of manufacturing them.

The invention therefore relates—in a first embodiment—to a process for the manufacture of a solid dosage form which is rapidly dissolving in aqueous medium, which process comprises (a) preparing a powder or granulate consisting of
  (1) either the active substance—or part thereof—and all other ingredients of the solid dosage form; or
  (2) all other ingredients of the solid dosage form except the active substance;
(b) dispensing
  (1) either an auxiliary solvent or
  (2) a solution or dispersion (preferably a solution) of the active substance in an auxiliary solvent,
in moulds or in the cavities of the pre-formed container intended for storage of the solid dosage form;
(c) compacting a suitable amount of the powder or granulate prepared according to (a)(1) or (a)(2) above;
(d) putting the compacted powder or granulate so obtained on the top of the liquid which according to (b)(1) or (b)(2) is in moulds or in the cavities of the pre-formed container intended for storage of the solid dosage form;
(e) removing the auxiliary solvent by applying a drying system to the units in the moulds or in the cavities of the pre-formed container intended for storage of the solid dosage form; and
(f) removing the dried units from the moulds into a suitable storage container or sealing the cavities of the pre-formed container intended for storage of the solid dosage form, respectively.

It will be understood that the order in which certain steps of this process are carried out is not fixed but interchangeable. For example, (b) may be carried out before (a), or (c) before (b). All these variations are intended to be covered by the present invention.

A preferred embodiment of the invention is characterized by the process for the manufacture of a solid, rapidly dissolving pharmaceutical or veterinary dosage form for oral administration, which process comprises (a) preparing a powder or granulate consisting of
  (1) either the intended dose of the active substance—or part thereof—and all other ingredients of the solid dosage form; or
  (2) all other ingredients of the solid dosage form except the active substance;
(a') transferring said powder or granulate to a combined compacting/dosing system;
(a") placing moulds or a pre-formed container intended for storage of the solid pharmaceutical or veterinary dosage form within the operating range of the combined compacting/dosing system;
(b) dispensing,
  (1) either an auxiliary solvent or
  (2) a solution or dispersion (preferably a solution) of the active substance in an auxiliary solvent, in moulds or in the cavities of the pre-formed container intended for storage of the solid pharmaceutical or veterinary dosage form;

(c) compacting—within the combined compacting/dosing system—a suitable amount of the powder or granulate prepared according to (a)(1) or (a)(2) above;

(d) putting the compacted powder or granulate on the top of the liquid which according to (b)(1) or (b)(2) is in moulds or in the cavities of the pre-formed container intended for storage of the solid pharmaceutical or veterinary dosage form;

(e) removing the auxiliary solvent by applying a drying system comprising one or more techniques selected from forced warm gas, microwave radiation and reduced pressure, to the units in the moulds or in the cavities of the pre-formed container intended for storage of the solid dosage form; and (f) removing the dried units from the moulds into a suitable storage container or sealing the cavities of the pre-formed container intended for storage of the solid pharmaceutical or veterinary dosage form, respectively.

In particular preferred is the process for the manufacture of a solid, rapidly dissolving pharmaceutical dosage form for oral administration, which process comprises (a) preparing a powder or granulate consisting of the active substance and all other ingredients of the solid dosage form;

(a') transferring said powder or granulate to a combined compacting/dosing system;

(a") placing a pre-formed container intended for storage of the solid pharmaceutical dosage form within the operating range of the combined compacting/dosing system;

(b) dispensing an auxiliary solvent in the cavities of the pre-formed container intended for storage of the solid pharmaceutical dosage form;

(c) compacting—within the combined compacting/dosing system—an amount of the powder or granulate prepared according to (a) above, which amount of powder or granulate contains the intended dose of the active substance;

(d) putting the compacted powder or granulate on the top of the liquid which according to (b) is in the cavities of the pre-formed container intended for storage of the solid pharmaceutical dosage form;

(e) removing the auxiliary solvent by applying a drying system comprising at least two different techniques selected from forced warm gas, microwave radiation and reduced pressure; and (f) sealing the cavities of the pre-formed container intended for storage of the solid pharmaceutical dosage form.

The active substance is typically used as the pure substance—which may be present e.g. in a certain crystalline form or in amorphous form—but it may also be e.g. microencapsulated, e.g. for the purpose of taste-masking, as a sustained release microencapsulation or a gastro-resistant microencapsulation (enteric coating); or in the form of a complex, e.g. a cyclodextrine complex or an ion exchange resin complex. It may be water-soluble or water-insoluble. Moreover, the active substance can e.g. be dissolved in an auxiliary solvent-wholly or only part thereof [see process variant (b)(2)]. Still another possibility is, for example, that the active substance together with some of the excipients is dissolved in an auxiliary solvent.

What the "other ingredients" of the solid dosage form is concerned [process step (a)], these are not critical and may vary within wide limits. The kind of ingredients used inter alia depends on the field where the solid dosage form is intended for, e.g. pharmaceuticals, veterinary products or other areas of application.

Preferably, the solid dosage form manufactured comprises (1) an active substance, (2) a filler and (3) a disintegration agent. Other usual excipients (4), like e.g. sweeteners, lubricants, flavours, taste-masking agents, binders, buffering agents, colouring agents, stabilisators or preservatives, may optionally be present.

The auxiliary solvent applied in step (b) is e.g. water, preferably purified water, or a non-aqueous solvent, e.g. ethanol, acetone or isopropanol, or any mixture of water with one or more of the non-aqueous solvents. Preferred are water, water/ethanol mixtures and ethanol; especially water and water/ethanol mixtures; and in particular water alone.

In step (b), the auxiliary solvent is dispensed in moulds or in the cavities of the pre-formed container by any means known in the art to be suitable for that purpose, e.g. a metered dose pump or a multi-pipette system.

In a preferred embodiment of the invention, the process steps (c) and (d) are accomplished with the aid of a combined compacting/dosing system.

In case that a combined compacting/dosing system is used, it must be able to serve the following functions: (a) dose a precise quantity of powder or granulate; (b) compact the dosed powder or dosed granulate; and (c) release the dosed compacted pellet.

In a preferred embodiment of the invention, the combined compacting/dosing system consists e.g. of a powder feed frame and an assembly of dosers capable of delivering a charge of the compacted drug powder in the desired dosage. The movements of the doser assembly and the feed frame can be driven e.g. pneumatically or electrically. The product powder or granules are prepared for dosing e.g. by a rotating paddle feed frame capable of regulating the depth of the powder bed. In a preferred embodiment of the invention, the doser assembly descends into the powder bed, takes and compacts the powder charges.

Then the doser assembly raises the dosed compacted drug powder from the powder bed and releases the dosed compacted powder charge intact into the moulds or the cavities of the preformed container, e.g. a blister pack.

After depositing the compacted powder into e.g. the blister cavities, the filled blister card is removed mechanically and replaced with an empty blister card so that the process may be repeated.

The system can also be adjusted so as to deliver a double-layer compacted powder into the cavities of the blister, where the first layer is intended for an immediate release (it disintegrates immediately in the mouth), and the second layer is for a sustained release (it softens in contact with saliva). In that case, the doser assembly may e.g. descend into a first powder bed, take up powder intended for the first layer, descend into a second powder bed, take up powder intended for the second layer, and finally compact the powder charges.

In a preferred embodiment, blisters (having several cavities) are filled by a doser/compaction assembly [process steps (c) and (d)]. In this case, the compaction system is e.g. composed of an assembly of dosers set up on a driven plate. Said doser/compaction assembly takes and compacts the powder in a powder feed vat. The thickness and density of the powder bed are ensured by a successive and automatic passage of a powder decompacting grid and leveling blade. Once the powder has been taken, the feed vat is replaced by the blister. Each cavity of the blister is placed under the doser/compaction assembly filled with compacted powder. A pellet of compacted powder is then deposited in each cavity of the blister, and the process starts again.

Removal of the auxiliary solvent [step (e)] is accomplished by applying a drying system which comprises one or more of the known drying techniques, e.g. warm forced gas, microwave or reduced pressure (vacuum). Preferably, at least two different techniques selected from forced warm gas, microwave radiation and reduced pressure are applied. Especially preferred are the combinations of forced warm gas together with microwave radiation and microwave radiation together with reduced pressure, in particular forced warm gas together with microwave radiation. Said combined techniques may be applied simultaneously or alternating (interchangeably), preferably simultaneously.

In a preferred embodiment of the invention, the auxiliary solvent is removed without applying any freeze-drying process in step (e).

The drying system may be static or dynamic. It may operate continuously or discontinuously during the drying process. Forced warm gas (e.g. air, nitrogen or carbon dioxide) has e.g. a temperature of from 30 up to 80° C. Forced warm gas is preferably forced warm nitrogen or forced warm air. Advantageously, it is heated before entering the drying system. It can be blown e.g. vertically or horizontally across the product. In case that the auxiliary solvent used comprises a solvent that may give rise to explosions when combined with oxygen and microwave radiation, e.g. ethanol, it is preferable to use non-oxygen-containing forced warm gas, e.g. nitrogen or carbon dioxide. But forced warm air may nevertheless be used, if the risk of explosion is avoided by other precautionary measures in the drying system. The risk of explosion can also be avoided in that case, if a drying system is used wherein microwave radiation is combined with reduced pressure (vacuum).

The microwave can be e.g. a mono-mode or multi-mode structure. When microwave radiation is applied, this is preferably done in a system that is able to work on-line (continuously) during the manufacturing process. Typically the wavelength of the microwave radiation is chosen so as to excite the solvent molecules, especially water, and expedite their evaporation. Advantageously, the microwave radiation is combined with forced warm gas which is capable of removing the humidity (gaseous water) generated.

"Reduced pressure" typically means pressures of from 0.1 mbar up to 500 mbar, and especially of from 20 to 200 mbar. The evaporation is typically performed at a temperature of from 20 up to 80° C., and preferably at 30–60° C. Said elevated temperatures are obtained e.g. by applying forced warm gas and/or microwave radiation.

In process step (f), it is preferred that the cavities of the pre-formed container intended for storage of the solid dosage form are sealed, e.g. with a lid. Pre-formed containers intended for storage of the solid dosage form are in particular blisters. Blisters are well-known in the art; they may be produced and formed from materials like e.g. polyvinyl chloride (PVC), PVC/polyvinylidene chloride (PVDC), PVC/Polyethylene (PE)/PVDC, PVC/PE/PVDC/PE/PVC, oriented polyamide (oPA)/Aluminium (Alu)/oPA or PVC/oPA/Alu/PVC.

In one special embodiment of the invention blisters are sealed with a lidding foil to obtain a peel off blister. Peel off (lidding) foils are composed of e.g. Paper/PETP(Polyethylene terephthalate)/Alu or Paper/PETP/Alu) or PETP/Alu.

From the description of the unique process of manufacture above it has become clear that the solid dosage form of the present invention is manufactured without applying any compression force to the mixture of its components (1), (2), (3) and optionally (4) during the last step of manufacture concerning the solid dosage form, i.e. process step (e). As a result of the particular process of manufacture used, the dosage form of the invention normally has a density of 300–1000 mg/ml, preferably of 400–900 mg/ml, and more preferably of 500–800 mg/ml, and especially of 500–700 mg/ml. This is a density that is much lower than that of compressed dosage forms like normal tablets etc. (having densities of above 1100 mg/ml). As a result of its unusually low density, the dosage form of the invention disintegrates more rapidly than would be the case, if the mixture of its components (1), (2), (3) and optionally (4) were subjected to compression force during the last step of manufacture concerning the solid dosage form, i.e. process step (e). When taken into the mouth, it typically disintegrates within 30 seconds, preferably within 20 seconds, more preferably within 10 seconds and most preferably within 8 seconds.

The invention therefore further relates to a solid dosage form which is rapidly dissolving in aqueous medium, which dosage form comprises
(1) an active substance,
(2) a filler, and
(3) a disintegration agent, which dosage form disintegrates when taken into the mouth within 30 seconds, and which dosage form has a density of 300–1000 mg/ml.

Preferred are solid pharmaceutical or veterinary solid dosage forms for oral administration consisting essentially of a homogeneous mixture of
(1) at least one pharmaceutically or veterinary active substance,
(2) at least one filler,
(3) at least one disintegration agent, and
(4) optionally other usual excipients,
which dosage form disintegrates when taken into the mouth within 30 seconds, and which dosage form has a density of 400–900 mg/ml.

In a preferred embodiment of the invention, the solid dosage forms mentioned herein before do contain at least one other usual excipient.

Further preferred are those solid pharmaceutical or veterinary dosage forms of the invention, wherein the composition contains as other usual excipients (4) a lubricant and optionally other usual excipients.

Especially preferred are those solid pharmaceutical or veterinary dosage forms of the invention, wherein the composition contains as other usual excipients (4) a lubricant, one or more sweeteners and optionally other usual excipients.

More precisely, the solid pharmaceutical or veterinary dosage form consists essentially of a mixture, especially a homogeneous mixture, of the components (1), (2), (3) and optionally (4) mentioned above.

The term "pharmaceutically active substance" is intended to be understood broadly so as to include not only pharmaceuticals but also e.g. vitamins, minerals, dietary supplements, nutritional supplements or infant formula products. Pharmaceuticals may include, without limitation, antacids, e.g. calcium or magnesium carbonate; analgesics, anti-inflammatories, antibiotics, laxatives, antidiarrheals, e.g. loperamide, anthelminthics; antifungals, e.g. terbinafine or a pharmaceutically acceptable salt thereof; emetics, antiemetics, anorexics, stimulants, antihaemorrhoids, antiasthmatics, antidiuretics, antiflatulents, antimigraine agents, antispasmodics, sedatives, antihyperactives, tranquilizers; antihistamines, e.g. loratidine; decongestants, e.g. pseudoephedrine or a pharmaceutically acceptable salt thereof; betablockers, hormones, weight-control substances and combinations thereof. Preferred active substances are analgesics and non-steroidal anti-inflammatory drugs, such as diclofenac, ketoprofen, ibuprofen, aspirin or paracetamol and pharmaceutically acceptable salts thereof, as well as hormones, e.g. melatonin. Minerals are e.g. pharmaceutically acceptable salts of calcium, magnesium or zinc, e.g. calcium carbonate, magenesium carbonate, magnesium L-aspartate or zinc gluconate.

Especially preferred is diclofenac which may be present either as free acid or as a pharmaceutically acceptable salt thereof, e.g. the potassium or sodium salt, and also diclofenac tromethamine salt or the diclofenac hydroxyethylpyrrolidinium salt, and also e.g. diclofenac complexes, e.g. diclofenac cyclodextrin complexes. In particular preferred is diclofenac potassium.

Another field of application of the solid dosage form according to the invention is the veterinary field, which concerns e.g. the protection of domestic animals or productive livestock against parasites that live in or on the animals, and the treatment of sick animals that are in need of a certain active substance.

The filler used can be any of those known in the art, e.g. mannitol, lactose, calcium phosphates, dibasic calcium phosphates, cellulose microcrystalline, cyclodextrine, starch, laevulose, maltitol, polydextrose, sucrose, glucose, inulin, sorbitol or xylitol. Preferred fillers are mannitol, lactose, sucrose, glucose, sorbitol, laevulose, microcrystalline cellulose and starch, and especially preferred are mannitol, lactose, starch and microcrystalline cellulose. It has been found that a particularly advantageous filler is mannitol, because it is particularly useful in forming the low density matrix of the dosage form that disintegrates rapidly within the mouth. Furthermore, mannitol is favourable in the drying process of the formulation [see step (e) of process hereinabove] because of its non-hygroscopic character. The filler is typically present in an amount of at least 30, preferably at least 50, more preferably at least 60, and especially at least 70 weight-% of the total dosage form.

The disintegration agent can be any of those known in the art, e.g., croscarmellose Na; sodium glycolates of starch, e.g., Explotab® and Primojel®; cross-linked poly-N-vinyl-2-pyrrolidones, e.g., Polyplasdone® XL and Kollidon® CL; polymethylmethacrylates, e.g., Eudispert® HV; polysaccharides, e.g., Emcosoy®; or synthetic resins, e.g., Amberlite® IRP88. Preferred disintegration agents are croscarmellose Na, sodium starch glycolate (e.g., Primojel®) and cross-linked poly-N-vinyl-2-pyrrolidones (especially Polyplasdone® XL). The disintegration agent is typically present in an amount of at least 1, preferably of at least 5, and especially of at least 10 weight-% of the total dosage form, e.g. of from 1 up to 20 weight-%, especially of from 1 up to 15 weight-%.

Lubricants which can optionally be present in the dosage form are e.g. talc, magnesium stearate, compritol® [corresponds to a behenic acid derivative, especially glyceryl behenate (also called "tribehenin") which corresponds to a mixture of glycerides (mainly triglycerides) of fatty acids (mainly behenic acid)]; polyethylene glycol, especially polyethylene glycol 6000, stearic acid, sodium stearyl fumarate, hydrogenated vegetable oil, sodium benzoate, L-leucine or silicon dioxide. If used, the lubricant is typically present in an amount of up to 10 weight-%, preferably up to 5 weight-%, e.g. in an amount of from 0.3 to 10 weight %, and especially in an amount of from 0.3 up to 5 weight-% of the total dosage form. Preferred as lubricant is talc.

Sweeteners which can optionally be present in the dosage form are e.g. sodium saccharin, aspartame, acesulfame K, neohesperidine (dihydrochalcone), thaumatin, miraculine or ammonium glycyrrhizinate. If used, the sweetener is typically present in an amount of up to 15 weight-% and especially in an amount of from 0.5 up to 15 weight-% of the total dosage form.

A combination of sweeteners which is of particular value for taste-masking of pharmaceutically active substances, especially of bitter active substances, e.g. diclofenac, terbinafine or pseudoephedrine or any pharmaceutically acceptable salts thereof, is characterized by the combination of (1) at least one of neohesperidine, thaumatin and ammonium glycyrrhizinate, (2) mint flavour and (3) at least one of aspartame and acesulfame or a pharmaceutically acceptable salt thereof, especially acesulfame K. Said combination of sweeteners combined with a pharmaceutically active substance, especially one requiring effective taste-masking, forms another embodiment of the invention.

Flavours (aromas) or taste-masking agents which can optionally be present in the dosage form are known in the art. Examples are sodium chloride, vanillin, citric acid, mint flavour, lemon flavour, orange flavour, grapefruit flavour, cream flavour, raspberry flavour, strawberry flavour, anise flavour or cherry flavour.

Binders which can optionally be present in the dosage form are e.g. polyvinylpyrrolidones, methyl hydroxypropyl cellulose and other cellulose materials, e.g. sodium carboxymethyl cellulose or hydroxypropyl cellulose, or gums, e.g. xanthan gum, guar gum, arabic gum, carrageenan, and, in particular, gellan gum.

If used, the binder is typically present in an amount of up to 10 weight-% and especially in an amount of from 0.5 up to 10 weight-% of the total dosage form.

Further excipients optionally present may be, for example, colorants, buffering agents, acidifying agents or preservatives.

According to the unique process of the invention, it is possible to provide solid dosage forms for a broad range of active ingredients with different physico-chemical parameters, for high dose unit forms (e.g. up to 1000 mg, in particular 500 mg of active substance) and also for combinations of active ingredients.

In the pharmaceutical (and veterinary) field, the solid dosage form is presented as a single dose unit, e.g. a tablet, of a size and shape adapted for direct oral administration to a patient (or a warm-blooded animal, respectively). The tablet is pleasant to take and, once placed into the mouth, will disintegrate substantially and instantly without any voluntary action by the patient, such as e.g. chewing. Upon disintegration of the tablet, the active ingredient is released and can be swallowed or is absorbed from the buccal cavity. Buccal absorption can be particularly advantageous for substances submitted to a high first hepatic metabolism. Drugs coming into consideration are in particular those with a relatively low molecular weight and pKa values enabling the presence of non-ionized drug at buccal pH.

In the pharmaceutical (and veterinary) field, the solid dosage form according to the present invention is convenient to use for the consumer (or warm-blooded animal, respectively) without the need of water or additional devices. Moreover, the instant disintegration and/or dissolution gives a sensation of a rapid and powerful action of the pharmaceutical dosage form and makes it unique and motivating for the patient to take.

The following examples illustrate the invention.

EXAMPLE 1

Fast Melting Oral Dosage Form Containing 12.5 mg of Diclofenac Potassium
(overall weight: 400 mg)

| Composition | mg/unit |
|---|---|
| Diclofenac K | 12.5 mg |
| Aspartame | 10 mg |
| Acesulfam K | 20 mg |
| Talc | 5 mg |
| Mint flavour | 10 mg |
| Croscarmellose Na | 25 mg |
| Mannitol | 317.5 mg |
| Total | 400 mg |

(a) All the components of the formulation are mixed for 5 min, sifted through a 0.5 mm mesh screen and then mixed again for 15 min. The homogeneous, dry mixture is filled into the feed frame of the combined compacting/dosing system, and the thickness and density of the powder bed are metered by a successive and automatic passage of a powder decompacting grid and leveling blade. (b) Each cavity of a pre-formed blister card is filled with 200 microliters of solvent (a mixture of water/ethanol 1:1) with the aid of multi-pipette system. For steps (c) and (d), a combined compacting/dosing system is used which consists of a powder feed frame and an assembly of dosers capable of delivering charges of compacted drug powder in the desired dosage. The assembly of dosers is composed of several compaction dispensers set up on a driven plate. Said assembly of dosers descends, takes and compacts the powder charges in a powder feed vat (step c). The assembly raises the dosed compacted powder from the powder bed and releases them intact into the cavities of the pre-formed blister card (filled with solvent before) (step d). After depositing the dosed compacted powder, the assembly raises again. The filled blister card is removed and transferred to an oven, and the process may be repeated. (e) The unit forms in the blisters are dried in an oven wherein forced warm nitrogen (T=50° C.) and microwave radiation are applied simultaneously for 45 minutes. (f) The dry blisters are sealed with a lidding foil (Paper/PETP/Aluminium).

In an analogous manner as described in example 1, also the fast melting oral dosage forms of examples 2–6 are manufactured.

EXAMPLE 2

| | |
|---|---|
| Calcium carbonate | 600 mg |
| Acesulfame K | 8 mg |
| Croscarmellose Na | 10 mg |
| Gellan gum | 20 mg |
| Lemon flavour | 10 mg |
| Cream flavour | 6 mg |
| Mannitol | 346 mg |
| Total | 1000 mg |

EXAMPLE 3

| | |
|---|---|
| Terbinafine hydrochloride | 60 mg |
| Neohesperidine | 1 mg |
| Acesulfame K | 30 mg |
| Sodium chloride | 5 mg |
| Croscarmellose Na | 30 mg |
| Talc | 5 mg |
| Mint flavour | 15 mg |
| Cream flavour | 5 mg |
| Mannitol | 249 mg |
| Total | 400 mg |

EXAMPLE 4

| | |
|---|---|
| Pseudoephedrine hydrochloride | 10 mg |
| ammonium glycyrrhizinate | 5 mg |
| Acesulfame K | 40 mg |
| Sodium chloride | 5 mg |
| Polyplasdone XL | 65 mg |
| Talc | 5 mg |
| Citric acid | 10 mg |
| Cream flavour | 5 mg |
| Mint flavour | 30 mg |
| Mannitol | 625 mg |
| Total | 800 mg |

EXAMPLE 5

| | |
|---|---|
| Magnesium L aspartate | 535 mg |
| Aspartame | 5 mg |
| Acesulfame K | 5 mg |
| Croscarmellose Na | 30 mg |
| Polyplasdone XL | 50 mg |
| Talc | 5 mg |
| Raspberry flavour | 10 mg |
| Citric acid | 7 mg |
| Mannitol | 353 mg |
| Total | 1000 mg |

EXAMPLE 6

| | |
|---|---|
| Zinc gluconate | 35 mg |
| Acesulfame K | 10 mg |
| Gellan gum | 10 mg |
| Croscarmellose Na | 20 mg |
| Talc | 5 mg |
| Raspberry flavour | 10 mg |
| Mannitol | 310 mg |
| Total | 400 mg. |

The invention claimed is:
1. A process for the manufacture of a solid dosage form which is rapidly dissolves in aqueous medium, wherein the solid dosage form comprises an active substance and other pharmaceutical ingredients suitable for a pharmaceutical or veterinary dosage form for oral administration, which process comprises
- (a) preparing a powder or granulate consisting of
  - (1) either the active substance or part thereof and the other pharmaceutical ingredients of the solid dosage form, or
  - (2) the other pharmaceutical ingredients of the solid dosage form;
- (b) dispensing
  - (1) either an auxiliary solvent, if (a)(1) includes all of the active substance, or
  - (2) a solution or dispersion of the active substance in an auxiliary solvent, in cavities of a pre-formed container intended for storage of the solid dosage form or molds;
- (c) compacting a suitable amount of the powder or granulate prepared according to (a)(1) or (a)(2) above;
- (d) putting the compacted powder or granulate prepared according to (c) on the top of the solvent which according to (b)(1) or (b)(2) is in the molds or in the cavities of the pre-formed container intended for storage of the solid dosage form;
- (e) removing the auxiliary solvent by applying a drying system to the molds or the cavities of the pre-formed container intended for storage of the solid dosage form after (d); and
- (f) removing the dried solid dosage form from the molds into a suitable storage container or sealing the cavities of the pre-formed container intended for storage of the solid dosage form, respectively, wherein the manufactured solid pharmaceutical or veterinary dosage form for oral administration is in the form of a tablet, and wherein in step (c) the suitable amount of the powder or granulate which is subjected to compaction contains an intended dose of the active substance.

2. A process according to claim 1 for the manufacture of a solid, rapidly dissolving pharmaceutical or veterinary dosage form for oral administration, which process comprises
- (a) preparing a powder or granulate consisting of
  - (1) either the intended dose of the active substance or part thereof and the other pharmaceutical ingredients of the solid dosage form, or
  - (2) the other pharmaceutical ingredients of the solid dosage form;
- (a') transferring the powder or granulate to a combined compacting/dosing system; and
- (a") placing the molds or the pre-formed container intended for storage of the solid pharmaceutical or veterinary dosage form within the operating range of the combined compacting/dosing system,
- (b) dispensing,
  - (1) either an auxiliary solvent, if (a)(1) includes all of the active substance, or
  - (2) a solution or dispersion of the active substance in an auxiliary solvent, in the molds or in the cavities of the pre-formed container intended for storage of the solid pharmaceutical or veterinary dosage form;
- (c) compacting—within the combined compacting/dosing system—a suitable amount of the powder or granulate prepared according to (a)(1) or (a)(2) above;
- (d) putting the compacted powder or granulate on the top of the liquid which according to (b)(1) or (b)(2) is in the molds or in the cavities of the pre-formed container intended for storage of the solid pharmaceutical or veterinary dosage form;
- (e) removing the auxiliary solvent by applying a drying system comprising one or more techniques selected from the group consisting of forced warm gas, microwave radiation and reduced pressure, to the units in the moulds or in the cavities of the pre-formed container intended for storage of the solid dosage form; and
- (f) removing the dried units from the moulds into a suitable storage container or sealing the cavities of the pre-formed container intended for storage of the solid pharmaceutical or veterinary dosage form, respectively.

3. A process according to claim 1 for the manufacture of a solid, rapidly dissolving pharmaceutical dosage form for oral administration, which process comprises
- (a) preparing a powder or granulate consisting of the active substance and the other pharmaceutical ingredients of the solid dosage form;
- (a') transferring the powder or granulate to a combined compacting/dosing system;
- (a") placing a pre-formed container intended for storage of the solid pharmaceutical dosage form within the operating range of the combined compacting/dosing system;
- (b) dispensing an auxiliary solvent in the cavities of the pre-formed container intended for storage of the solid pharmaceutical dosage form;
- (c) compacting—within the combined compacting/dosing system—an amount of the powder or granulate prepared according to (a) above, which amount of powder or granulate contains the intended dose of the active substance;
- (d) putting the compacted powder or granulate on the top of the liquid which according to (b) is in the cavities of the pre-formed container intended for storage of the solid pharmaceutical dosage form;
- (e) removing the auxiliary solvent by applying a drying system comprising at least two different techniques selected from the group consisting of forced warm gas, microwave radiation and reduced pressure; and
- (f) sealing the cavities of the pre-formed container intended for storage of the solid pharmaceutical dosage form.

4. A process according to claim 1, where in step (b) the auxiliary solvent is selected from the group consisting of water, ethanol, acetone, isopropanol and any mixtures thereof.

5. A process according to claim 1, wherein the density of the solid dosage form is between 300 and 1000 mg/ml.

6. A process according to claim 1, wherein the density of the solid dosage form is between 400 and 900 mg/ml.

7. A process according to claim 1, where in step (e) the auxiliary solvent is removed by applying simultaneously or sequentially at least two different techniques selected from the group consisting of forced warm gas, microwave radiation and reduced pressure.

8. A process according to claim 1, where in step (e) the auxiliary solvent is removed by applying simultaneously a combination of forced warm gas and microwave radiation.

9. A process for the manufacture of a solid dosage pharmaceutical composition which rapidly dissolves in an aqueous medium wherein the density of the solid dosage pharmaceutical composition is between 300 and 1000 mg/ml, said process comprising the steps of
- (a) preparing solid powder or granule forms of ingredients for the solid dosage composition, the ingredients including an active substance;
- (b) compacting a suitable amount of the ingredients including none, some or all of the active substance;

(c) dispensing in a mold or a cavity of a pre-formed container intended for storage of the solid dosage composition either an auxiliary solvent or an active substance-containing auxiliary solvent if the compacting step (b) does not include all of the active substance, wherein the active substance-containing auxiliary solvent is a solution or suspension of the active substance in the auxiliary solvent;

(d) placing the compacted solid ingredients in the mold or cavity; and (e) removing the auxiliary solvent from the mold or cavity to form the solid dosage composition after the compacted solid ingredients and the auxiliary solvent with or without the active substance are placed therein, wherein the manufactured solid pharmaceutical dosage form is for oral administration in a form of a tablet, and wherein in step (b) the suitable amount of the powder or granulate which is subjected to compaction contains an intended dose of the active substance.

* * * * *